(12) United States Patent
Ray, II

(10) Patent No.: US 12,343,345 B2
(45) Date of Patent: *Jul. 1, 2025

(54) NON-INFECTIVE NASAL SYMPTOM MANAGEMENT COMPOSITIONS AND METHODS

(71) Applicant: CMPD LICENSING, LLC, Conroe, TX (US)

(72) Inventor: Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 976 days.

This patent is subject to a terminal disclaimer.

(21) Appl. No.: 17/460,693

(22) Filed: Aug. 30, 2021

(65) Prior Publication Data

US 2021/0386748 A1 Dec. 16, 2021

Related U.S. Application Data

(63) Continuation-in-part of application No. 16/167,108, filed on Oct. 22, 2018, now Pat. No. 11,701,426, and a continuation-in-part of application No. 16/167,131, filed on Oct. 22, 2018.

(51) Int. Cl.

| | | |
|---|---|---|
| *A61K 31/522* | (2006.01) | |
| *A61K 9/00* | (2006.01) | |
| *A61K 31/194* | (2006.01) | |
| *A61K 31/58* | (2006.01) | |
| *A61K 47/26* | (2006.01) | |

(52) U.S. Cl.
CPC .......... *A61K 31/522* (2013.01); *A61K 9/0043* (2013.01); *A61K 31/194* (2013.01); *A61K 31/58* (2013.01); *A61K 47/26* (2013.01)

(58) Field of Classification Search
CPC ................ A61K 31/522; A61K 9/0043; A61K 31/194; A61K 31/58; A61K 47/26
See application file for complete search history.

(56) References Cited

U.S. PATENT DOCUMENTS

| | | | |
|---|---|---|---|
| 4,003,884 | A | 1/1977 | Konig |
| 4,454,140 | A | 6/1984 | Goldberg |
| 6,598,603 | B1 | 7/2003 | Andersson |
| 2008/0045564 | A1 | 2/2008 | Roberts |
| 2011/0150992 | A1 | 6/2011 | Arnold |
| 2014/0377357 | A1 | 12/2014 | Banov |

FOREIGN PATENT DOCUMENTS

| | | |
|---|---|---|
| CN | 101347436 | 1/2009 |
| WO | 2009066262 | 5/2009 |
| WO | 2014205159 | 12/2014 |

OTHER PUBLICATIONS

Evans et al (Year: 1997).*
US Pharmacist, Anosmia, US Pharm. Vol. 36(1), pp. 17-18, 2011.
Mott et al., Topical corticosteroid treatment of anosmia associated with nasal and sinus disease, Arch. Otolaryngol. Head Neck Surg., col. 123(4), pp. 367-372, 1997.
The Asthma Center, Smell loss promising New Treatment, Mar. 29, 2017.
Wang et al., Comparison of inhaled corticosteroid combined with theophylline and double-dose inhaled corticosteroid in moderate to severe asthma, Respirology, Mar. 31, 2005.
Cafasso, What is Anosmia?, Updated Aug. 29, 2019.
May et al., Management of allergic rhinitis: A review for the community pharmacist, Clin. Therapeutics, vol. 39(12), pp. 2410-2419, 2017.
Medline Plus Drug Information, Methylprednisolone, rev. Sep. 15, 2017.
Yuzkat et al., Effects of theophylline with methylprednisolone combination therapy on biomechanics and histopathology in diaphragm muscles of rats, inflammation, vol. 39(5), pp. 1635-1641, 2016.
Colak et al., Sugammadex-induced Hypersensitivity Reaction in a Pediatric Patient, Turk J. Anaesthesiol. Reanim., vol. 46, pp. 66-68, Feb. 2018.
TGMEDS Home of the Hormones 2016 Document, Rhinitis: diagnosis and treatment, http://www.Tgmeds.org.uk/rhinitis-diagnosis-and-treatment.html), 2005.
Kook et al., Increased expression of bitter taste receptors in human allergic nasal mucosa and their contribution to the shrinkage of human nasal mucosa, Clinical & Experimental Allergy, vol. 46, pp. 584-601, 2016.
Munch et al., A Comparative Study of Dexchlorpheniramine Maleate Sustained Release Tablets and Budesonide Nasal Spray in Seasonal Allergic Rhinitis, Allergy, vol. 38, pp. 517-524, 1983.
El-Gendy et al., Development of Budesonide NanoCluster Dry Powder Aerosols: Formulation and Stability, J. of Pharmaceutical Sciences, vol. 101(9), pp. 3445-3455, Sep. 2012.
Whiteman, Cancer cell growth halted with cold and flu drug, Medical News Today, 2017.
Hematology Oncology Associates of Fredericksburg, Common Cod., 2016.
Best Practice Journal, Cold Season in primary care: Advice is the best medicine, vol. 52, pp. 26-33, 2013.
Yousefichaijan et al., The effect of zinc sulfate on duration of common cold symptoms in children, J. Biology and Today's World, vol. 6(10), pp. 186-190, 2017.
Litak, Jason, Should you put some zinc in that stuffy nose?, Nutrition Noteworthy, vol. 7(1), 2005.
Fashner et al., Treatment of the common cold in children and adults, American Family Physician, vol. 86(2), pp. 153-159, 2012.

* cited by examiner

*Primary Examiner* — Jeffrey S Lundgren
*Assistant Examiner* — Ibrahim D Bori
(74) *Attorney, Agent, or Firm* — Akerman LLP

(57) ABSTRACT

A method of managing non-infective nasal symptoms may include formulating a topical composition for nasal administration. The formulation may include theophylline and sodium citrate. The formulation may also include a steroid, such as budesonide. The topical composition may be administered nasally.

17 Claims, No Drawings

NON-INFECTIVE NASAL SYMPTOM MANAGEMENT COMPOSITIONS AND METHODS

This application is a continuation-in-part of U.S. patent application Ser. Nos. 16/167,108 and 16/167,131, both of which were filed Oct. 22, 2018. U.S. patent application Ser. No. 16/167,108 and U.S. patent application Ser. No. 16/167,131 are hereby incorporated by reference herein.

FIELD OF THE TECHNOLOGY

The present disclosure is directed to topical composition and related methods of treating non-infective nasal symptoms.

BACKGROUND

Respiratory tract conditions are extremely common ailments of the human experience and include rhinologic conditions, infections, and other obstructions to respiration. One reason for this frequency is constant exposure of respiratory surfaces to the external environment. For example, foreign matter such as debris, microorganisms, viruses, biological matter, and even harsh environmental conditions may enter the body during respiration, irritating or infecting respiratory tract surfaces or even the internal body. Overtime, the human body has also evolved defenses designed to protect the body from this exposure. These defenses include mucous lining and immune responses such as inflammation and increased mucous production or viscosity. Diseases and abnormalities such as chronic obstructive pulmonary disease (COPD), asthma, rhinitis, and various allergies may also include undesirable triggering or modulation of such defenses, e.g., excessive immune responses that cause bronchoconstriction or excessive mucous production or thickening.

Often times an initial treatment objective of respiratory tract conditions is to relieve the obstruction and restore unobstructed respiration by increasing drainage or relieving inflammation. Further objectives may be directed to relieving discomfort or treating the underlying condition. Treatments may include localized application or action of medications, e.g., using nasal spray or metered inhaler. However, respiratory tract conditions may manifest at multiple locations complicating targeted delivery of medication where needed, thus, systemic delivery routes such as oral or intravenous administration, have also been used. Causes of respiratory tract conditions are also numerous and identification of a precise cause may be difficult, especially when multiple conditions are present.

SUMMARY

In one aspect, a method of formulating a topical composition for nasal administration to manage non-infective nasal symptoms includes combining theophylline, sodium citrate, an aqueous diluent, and xylitol and/or poloxamers. For each unit dose in the topical composition, the topical composition may include the sodium citrate in an amount between about 20 mg and about 200 mg, the theophylline in an amount between about 5 mg and about 150 mg, and the xylitol and/or poloxamers in a combined amount between about 50 mg and about 400 mg.

In one example, the method includes combining budesonide. The budesonide may be combined in an amount between about 1 mg and about 4 mg per unit dose in the topical composition. In a further example, combining the budesonide includes adding contents of one or more budesonide 0.5 mg-2 ml inhalation suspension vials and/or budesonide 1 mg-2 ml inhalation suspension vials. In one example, the diluent is distilled water.

In one example, the topical composition includes between about 10 mg and about 100 mg sodium citrate per unit dose in the topical composition. The topical composition may also include between about 50 mg and about 150 mg theophylline per unit dose in the topical composition. The topical composition may include between about 100 mg and about 300 mg xylitol and/or poloxamers per unit dose in the topical composition. The topical composition may also include budesonide. The budesonide may be combined in an amount between about 1 mg and about 4 mg per unit dose in the topical composition. Combining the budesonide may include adding the contents of one or more budesonide 0.5 mg-2 ml inhalation suspension vials and/or budesonide 1 mg-2 ml inhalation suspension vials.

In another aspect, a topical composition for nasal administration to manage non-infective nasal symptoms includes theophylline in an amount between about 20 mg and about 200 mg per unit dose of the topical composition; sodium citrate in an amount between about 5 mg and about 150 mg per unit dose of the topical composition; and xylitol and/or poloxamers in a combined amount between about 50 mg and about 400 mg.

In one example, the topical composition also includes budesonide. The budesonide may be present in an amount between about 1 mg and about 4 mg per unit dose of the topical composition.

In an above or another example, the sodium citrate is present in an amount between about 10 mg and about 100 mg per unit dose of the topical composition.

In an above or another example, the theophylline is present in an amount between about 50 mg and about 150 mg per unit dose of the topical composition.

In an above or another example, the xylitol and/or poloxamers are present in an amount between about 100 mg and about 300 mg per unit dose of the topical composition.

DESCRIPTION

The present disclosure describes topical compositions and related methods of treating, e.g., managing, non-infective nasal symptoms. The topical compositions may be formulated for nasal delivery such as irrigation or nebulization, for example. In some applications, the topical compositions may be nasally administered to patients with non-infective nasal issues or medical conditions, which are issues or conditions that are not the caused by an infection.

In some embodiments, a topical composition disclosed herein may be used as a supplemental or replacement therapy for patients who are currently using nasally delivered steroids, nasally or orally delivered antihistamines, nasally delivered anticholinergics, nasally or orally delivered mucolytics, orally delivered montelukast, or irrigation systems to clear out the nasal cavities and remove debris. While the topical composition may be formulated for treatment of symptoms generally associated with non-infective nasal conditions.

Various embodiments of the topical composition may be used to treat non-infective nasal conditions (not caused by an infection) or symptoms of non-infective conditions such as one or more of inflammation in the nasal cavity, thick-mucus secretions in nasal cavity, allergic rhinitis (runny nose), anosmia (inability to smell), or other nasal conditions or related symptoms caused by non-infective conditions.

Embodiments of the topical composition may include various components including active agents, bases, carriers, excipients, solubilization agents, dispersion agents, emulsifiers, diluents, flavoring agents, pH adjusting agents, fillers, or the like.

The topical composition and associated methods of treatment may include a pharmaceutically effective amount of an active component, which those having skill in the art will appreciate may include salts, pharmaceutical equivalents, or derivatives thereof. For brevity, however, such salts, equivalents, and derivatives may be referred to herein with respect to the active agent or class of active agent. For example, the composition may comprise azelastine, which is intended to include an equivalent pharmaceutically effective amount of azelastine hydrochloride.

Various embodiments of the topical composition may include an active component selected from one or more of a steroid, antihistamine, anticholinergic, mucolytic, or combinations thereof.

One or more steroids of an active component may include a corticosteroid, glucocorticoid steroid, or both, for example. Corticosteroids mimic the effects of hormones that the body produces naturally in your adrenal glands. Corticosteroids can suppress inflammation and can reduce the signs and symptoms of inflammatory conditions (e.g., arthritis and asthma). Corticosteroids can also suppress the immune system. Corticosteroids can act on a number of different cells (e.g., mast cells, neutrophils, macrophages and lymphocytes) and a number of different mediators (e.g., histamine, leukotriene, and cytokine subtypes).

In various embodiments, the topical composition may include one or more steroids selected from triamcinolone (e.g., diacetate, hexacetonide, and acetonide), betamethasone (e.g., dipropionate, benzoate, sodium phosphate, acetate, and valerate), dexamethasone (e.g., dipropionate and valerate), flunisolide, prednisone (e.g., acetate), prednisolone (e.g., acetate, sodium phosphate, and tebutate), methylprednisolone (e.g., acetate and sodium succinate), fluocinolone (e.g., acetonide), budesonide, diflorasone (e.g., diacetate), halcinonide, desoximetasone (desoxymethasone), diflucortolone (e.g., valerate), flucloronide (fluocortolone acetonide), fluocinonide, fluocortolone, fluprednidene (e.g., acetate), flurandrenolide (flurandrenolone), clobetasol (e.g., propionate), clobetasone (e.g., butyrate), alclometasone, flumethasone (e.g., pivalate), fluocortolone (e.g., hexanoate), amcinonide, beclomethasone (e.g., dipropionate), fluticasone (e.g., propionate), difluprednate, prednicarbate, flurandrenolide, mometasone, and desonide.

In various embodiments, the topical composition includes one or more of the above steroids in an amount about 0.25 mg to about 10 mg, such as about 0.5 mg to about 8 mg, about 1 mg to about 6 mg, about 2 mg to about 5 mg, about 3 mg to about 5 mg, about 4 mg to about 6 mg, about 5 mg to about 7 mg, about 6 mg to about 9 mg, about 6 mg to about 10 mg, about 0.25 mg to about 5 mg, about 0.5 mg to about 5 mg, about 0.5 mg to about 3 mg, about 0.5 to about 2 mg, about 2 mg to about 3 mg, about 3 mg to about 4 mg, about 0.25 mg, about 0.5 mg, about 1 mg, about 2 mg, about 3 mg, about 4 mg, about 5 mg, about 6 mg, or about 7 mg. The amounts of actives, excipients, diluent, and other components disclosed herein with respect to the topical composition may refer to unit or administration dose amounts, which represents the amount of the ingredient in a dose of the topical composition that is to be administered to the subject. As noted herein, the topical composition may include diluents or other ingredients that increase the total amount of matter in an administration dosage. Thus, the weight or volume of an unit dose may vary. For example, a nasal irrigation format may include additional diluent than a nebulization format. Those having skill in the art may determine suitable weights, volumes, and corresponding amounts of diluent suitable for the route of administration.

In one embodiment, the steroid comprises or consists of fluticasone. For example, the topical composition may include fluticasone in an amount about 0.5 mg to about 6 mg, about 1 mg to about 5 mg, about 2 mg to about 4 mg, about 2 mg to about 3 mg, about 3 mg to about 4 mg, or about 3 mg.

In one embodiment, the steroid comprises or consists of budesonide. For example, the topical composition may include budesonide in an amount about 0.25 mg to about 4 mg, about 0.25 mg to about 3 mg, about 0.25 mg to about 2 mg, about 0.5 mg to about 2 mg, about 0.5 to about 1 mg, about 1 mg to about 2 mg, about 0.5 mg, about 1 mg, or about 2 mg.

In one embodiment, the steroid comprises or consists of methylprednisolone. For example, the topical composition may include methylprednisolone in an amount about 1 mg to about 10 mg, about 2 mg to about 9 mg, about 3 mg to about 8 mg, about 4 mg to about 7 mg, about 4 mg to about 6 mg, about 4 mg to about 5 mg, about 4 mg, about 5 mg, about 6 mg, or about 8 mg. The methylprednisolone may include a methylprednisolone solution, suspension, emulsion, or powder.

As introduced above, the topical composition may include an active component comprising one or more antihistamines. Antihistamines act to reduce or block histamine receptors (e.g., H1 receptors and H2 receptors). When included, antihistamines may comprise or consist of, but are not limited to, one or more of the following: acrivastine, azelastine, bilastine, bromodiphenhydramine, brompheniramine, buclizine, carbinoxamine, cetirizine, chlorodiphenhydramine, chlorphenamine, chlorpheniramine, chlorpromazine, cimetidine, clemastine, cyclizine, cyproheptadine, desloratadine, dexbrompheniramine, dexchlorpheniramine, dimenhydrinate, dimetindene, diphenhydramine, doxylamine, ebastine, embramine, emedastine, famotidine, fexofenadine, hydroxyzine, lafutidine, levocabastine, loratadine, meclozine, mirtazapine, nizatidine, olopatadine, orphenadrine, phenindamine, pheniramine, phenyltoloxamine, promethazine, pyrilamine, quetiapine, ranitidine, roxatidine, rupatadine, tiotidine, tripelennamine, or triprolidine.

In some embodiments, the topical composition includes an active component comprising or consisting of any of the steroids and associated amounts of the steroids, identified above or elsewhere herein, and one or more of the above antihistamines in an amount about 10 mg to about 1 g, about 10 mg to about 500 mg, about 15 mg to about 300 mg, about 25 mg to about 300 mg, about 50 mg to about 250 mg, about 75 mg to about 200 mg, about 100 mg to about 900 mg, about 200 mg to about 800 mg, about 300 mg to about 700 mg, about 400 mg to about 700 mg, or about 500 mg to about 800 mg. In one embodiment, the antihistamine comprises or consists of azelastine in an amount about 100 mg to 1000 mg, about 200 mg to about 900 mg, 300 mg to about 800 mg, 400 mg to about 700 mg, 400 mg to about 600 mg, 500 mg to about 600 mg, about 400 mg, about 500 mg, or about 500 mg. In some embodiments, the topical composition may include an antihistamine in addition to the steroid and one or more of an anticholinergic, mucolytic, theophylline, sodium citrate, anti-inflammatory, or leukotriene receptor antagonist disclosed herein.

As introduced above, the topical composition may include an active component comprising one or more anticholinergics. Anticholinergics act to block the action of the neurotransmitter acetylcholine in both the central and peripheral nervous systems. In various embodiments, the topical composition includes one or more anticholinergics comprising or consisting of atropine, belladonna alkaloids, benzatropine, benztropine mesylate, biperiden, bupropion, chlorpheniramine, clemastine, darifenacin, dextromethorphan, dicyclomine, dimenhydrinate, diphenhydramine, doxacurium, doxepin, doxylamine, fesoterodine, flavoxate, glycopyrrolate, hexamethonium, hydroxyzine, hyoscyamine, ipratropium (e.g., ipratropium bromide), mecamylamine, orphenadrine, oxitropium, oxybutynin, procyclidine, propantheline, scopolamine, solifenacin, tiotropium, tolterodine, trihexyphenidyl, tropicamide, tubocurarine, or a combination thereof.

In some embodiments, the topical composition comprises or consists of any of the steroids and associated amounts of the steroids, identified above or elsewhere herein, and one or more of the above anticholinergics in an amount about 0.01 mg to about 1 mg, about 0.01 mg to about 0.1 mg, about 0.02 mg to about 0.1 mg, about 0.03 mg to about 0.1 mg, about 0.05 mg to about 0.6 mg, about 0.08 mg to about 0.5 mg, about 0.1 to about 0.5 mg, or about 0.5 mg to about 1 mg. In one embodiment, the anticholinergic comprises ipratropium. In some embodiments, the topical composition may include an anticholinergic in addition to the steroid and one or more of an antihistamine, mucolytic, theophylline, sodium citrate, anti-inflammatory, or leukotriene receptor antagonist disclosed herein.

As introduced above, the topical composition may include an active component comprising one or more mucolytics. Mucolytics loosen and clear mucus from the airways. The topical composition may include one or more mucolytics comprising or consisting of acetylcysteine, bromheksin, carbocysteine, erdosteine, guiafenesin, and iodinated glycerol, or pharmaceutically acceptable salts thereof, or a combination thereof.

In some embodiments, the topical composition includes an active component comprising or consisting of any of the steroids and associated amounts of the steroids, identified above or elsewhere herein, and one or more of the above mucolytics in an amount about 5 mg to about 500 mg, about 15 mg to about 400 mg, about 50 mg to about 300 mg, about 75 mg to about 200 mg, about 75 mg to about 150 mg, about 100 mg to about 250 mg, about 200 mg to about 500 mg. In some embodiments, the topical composition may include a mucolytic in addition to the steroid and one or more of an antihistamine, anticholinergic, theophylline, sodium citrate, anti-inflammatory, or leukotriene receptor antagonist. In one embodiment, the mucolytic comprises acetylcysteine in an amount about 15 mg to about 250 mg, about 25 mg to about 200 mg, about 50 mg to about 150 mg, about 75 mg to about 125 mg, or about 100 mg.

In various embodiments, the topical composition includes an active component including theophylline. Theophylline acts as a phosphodiesterase inhibitor, adenosine receptor blocker, and histone deacetylase activator. Mechanism of action of Theophylline appears to stem from smooth muscle relaxation (bronchodilation) and suppression of the response of the airways to stimuli (i.e. non-bronchodilator prophylactic effects). In some embodiments, the topical composition comprises of consists of any of the steroids and associated amounts of the steroids identified above and elsewhere herein and theophylline in an amount about 15 mg to about 250 mg, about 25 mg to about 200 mg, about 50 mg to about 150 mg, about 75 mg to about 125 mg, or about 100 mg. In some embodiments, the topical composition may include theophylline in addition to the steroid and one or more of sodium citrate, an antihistamine, a mucolytic, an anticholinergic, an anti-inflammatory, or a leukotriene receptor antagonist disclosed herein.

In various embodiments, the topical composition may include a component comprising or consisting of sodium citrate. Sodium citrate may include monosodium citrate, disodium citrate, or preferably trisodium citrate or more preferably sodium citrate dihydrate. In some embodiments, the topical composition includes sodium citrate and any of the steroids and associated amounts of the steroids identified above and elsewhere herein and/or theophylline, wherein the sodium citrate is present in an amount about 5 mg to about 150 mg, about 10 mg to about 100 mg, about 10 mg to about 75 mg, about 25 mg to about 50 mg, about 50 mg to about 75 mg, about 50 mg to about 100 mg, or about 75 mg to about 100 mg. In some embodiments, the topical composition may include sodium citrate and theophylline in addition to a steroid and one or more of an antihistamine, mucolytic, anticholinergic, anti-inflammatory, or leukotriene receptor antagonist disclosed herein.

As introduced above, in some embodiments, the topical composition may include an active component comprising one or more anti-inflammatories. The anti-inflammatory may comprise or consist of hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide, and non-steroidal anti-inflammatories (NSAIDs) such as salicylate, indomethacin, ibuprofen, diclofenac, flurbiprofen, piroxicam indomethacin, ibuprofen, naxopren, piroxicam and nabumetone. In some embodiments, the topical composition may include any of the steroids and associated amounts of the steroids identified above and elsewhere herein and about 10 mg to about 200 mg anti-inflammatory. In some embodiments, the topical composition may include an anti-inflammatory in addition to the steroid and one or more of an antihistamine, mucolytic, anticholinergic, theophylline, sodium citrate, or leukotriene receptor antagonist disclosed herein.

In various embodiments, the topical composition may include an active component comprising one or more leukotriene receptor antagonists. Leukotriene receptor antagonist function as a leukotriene-related enzyme inhibitor or a leukotriene receptor antagonist to oppose the function of these inflammatory mediators. The leukotriene receptor antagonists may comprise or consist of one or more of montelukast, zafirlukast, zilueton, or a combination thereof. In some embodiments, the topical composition may include any of the steroids and associated amounts of the steroids identified above and elsewhere herein and a one or more of a leukotriene receptor antagonist, an antihistamine, mucolytic, anticholinergic, theophylline, sodium citrate, or anti-inflammatory disclosed herein.

The topical composition may include an active agent component comprising quinine sulfate. Quinine sulfate may include equivalent amounts of active substance from quinine or other quinine salts such as quinine hydrochloride, quinine di-hydrochloride, quinine sulfate dehydrate, quinine bisulfate, or quinine gluconate. Quinine sulfate is an antimalarial drug indicated only for treatment of uncomplicated Plasmodium falciparum malaria and has been shown to be effective in geographical regions where resistance to chloroquine has been documented. In some embodiments, the topical composition includes any of the steroids and associated amounts of the steroids identified above and elsewhere herein and quinine sulfate in an amount about 50 mg to about 1000 mg, about 50 mg to about 700 mg, about 100 mg to about 700 mg, about 200 mg to about 500 mg, about 300 mg to about 400 mg, about 300 mg to about 700 mg, about 400 mg to about 700 mg, about 500 mg to about 700 mg, about 600 mg to about 700 mg, or about 325 mg or about 650 mg. Quinine sulfate may be combined with any steroid herein. For example, quinine sulfate may be combined with one or more steroids wherein the one or more steroids are present in an amount about 0.25 mg to about 10 mg, such as about 0.5 mg to about 8 mg, about 1 mg to about 6 mg, about 2 mg to about 5 mg, about 3 mg to about 5 mg, about 4 mg to about 6 mg, about 5 mg to about 7 mg, about 6 mg to about 9 mg, about 6 mg to about 10 mg, about 0.25 mg to about 5 mg, about 0.5 mg to about 5 mg, about 0.5 mg to about 3 mg, about 0.5 to about 2 mg, about 2 mg to about 3 mg, about 3 mg to about 4 mg, about 0.25 mg, about 0.5 mg, about 1 mg, about 2 mg, about 3 mg, about 4 mg, about 5 mg, about 6 mg, or about 7 mg. In one embodiment, the steroid comprises or consists of fluticasone, e.g., about 0.5 mg to about 6 mg, about 1 mg to about 5 mg, about 2 mg to about 4 mg, about 2 mg to about 3 mg, about 3 mg to about 4 mg, or about 3 mg fluticasone. In one embodiment, the steroid comprises or consists of budesonide, e.g., for example, about 0.25 mg to about 4 mg, about 0.25 mg to about 3 mg, about 0.25 mg to about 2 mg, about 0.5 mg to about 2 mg, about 0.5 to about 1 mg, about 1 mg to about 1.5 mg, about 1.5 mg to about 2 mg, about 1 mg to about 2 mg, about 0.5 mg, about 1 mg, or about 2 mg budesonide. In one embodiment, the steroid comprises or consists of methylprednisolone, e.g., about 1 mg to about 10 mg, about 2 mg to about 9 mg, about 3 mg to about 8 mg, about 4 mg to about 7 mg, about 4 mg to about 6 mg, about 4 mg to about 5 mg, about 4 mg, about 5 mg, about 6 mg, or about 8 mg methylprednisolone.

Quinine sulfate is commercially available in capsules for oral administration. Such capsules may contain 324 mg of the active ingredient quinine sulfate USP, equivalent to 269 mg free base and inactive ingredients: corn starch, magnesium stearate, and talc. Quinine sulfate or quinine sulfate capsules may be available in other capsule strengths. In some embodiments, the topical composition may include in addition to the steroid and one or more of an antihistamine, mucolytic, anticholinergic, anti-inflammatory, or leukotriene receptor antagonist, sodium citrate, or theophylline disclosed herein.

The topical composition may comprise one or more of the listed active or other components disclosed herein and one or more additional components including one or more pharmaceutically acceptable excipients. In other embodiments, however, the formulations consist of the one or more of the listed ingredients and one or more pharmaceutically acceptable excipients. Exemplary excipient components may assist in the release, dispersion, solubility, and/or the delivery of one or more of the active components or modify taste. For example, excipients may include one or more of diluents, dispersants, preservatives, solvents, co-solvents, wetting agents, buffering agents, humectants, permeation enhancer, emollient, sweetening agents, anti-foaming agents, thickening agents, or flavoring agents, for example. Diluents may include water, distilled water, sterile water, water for injection, sodium chloride, or saline solution, for example. The diluent may comprise an aqueous diluent or non-aqueous diluent.

The topical composition may comprise a topical preparation formulated for application to an external or internal body surface such skin or mucosal surfaces of the respiratory tract. The topical compositions may be formulated to act at the tissue surface or absorb for local action. In some embodiments, however, the topical preparations may include an aspect of systemic action.

The topical composition may include an excipient component including xylitol, poloxamers, or both. The amount of xylitol and/or poloxamers included in the topical composition may be between about 10 mg and about 1 g, such about 50 mg to about 500 mg, about 100 mg to about 400 mg, or about 150 mg to about 300 mg. In various embodiments, the topical composition includes a product sold under the name LOXASPERSE®, manufactured by PCCA (Houston, TX), that includes xylitol and poloxamers.

In some embodiments, the topical composition includes an active component comprising or consisting of a steroid selected from fluticasone, budesonide, methylprednisolone, or combination thereof. For example, the steroid may comprise about 0.5 mg to about 6 mg fluticasone, about 0.25 mg to about 4 mg budesonide, or about 1 mg to about 10 mg methylprednisolone. In a further embodiment, the topical composition may comprise or consist of one or more steroids and sodium citrate in an amount about 10 mg to about 150 mg, such about 10 to about 50 mg, about 50 mg to about 100 mg, or about 25 mg. In the above or a further embodiment, the active component further comprises about 5 mg to about 150 mg, such as between about 50 mg to about 150 mg, about 75 mg to about 125 mg, or about 100 mg, theophylline. In one example, the topical composition may further include a diluent, e.g., as disclosed herein, such as an aqueous diluent, which may comprise or consist of water, distilled water, sterile water, water for irrigation, water for injection, saltwater, sodium chloride (e.g., 0.9%) or saline. In one formulation, the topical composition includes one or both of poloxamers or xylitol. For example, the combined amount of poloxamers and/or xylitol in the topical composition may be between about 10 mg and about 1 g, such as in an amount about 50 mg to about 500 mg, about 100 mg to about 400 mg, or about 150 mg to about 300 mg. In one example, poloxamers, xylitol, or mixture thereof may include LOXASPERSE®, which may be combined alone or in combination with one or more additional active ingredients. In one embodiment, the topical composition is configured for combination therapy wherein the steroid is administered separately from the theophylline and sodium citrate.

In one embodiment, the topical composition comprises about 0.5 mg to about 6 mg fluticasone, about 50 mg to about 150 mg, such as about 50 mg to about 125 mg, theophylline, and/or about 10 mg to about 125 mg, such as about 10 mg to about 100 mg, sodium citrate. The topical composition may also include about 10 mg to about 1 g antihistamine and/or about 5 mg to 500 mg mucolytic. In one example, the antihistamine comprises about 100 mg to about 1 g azelastine. In this or another example, the mucolytic comprises about 15 mg to about 250 mg acetylcysteine. In one example, the topical composition may further include a diluent, e.g., as disclosed herein, such as an aqueous diluent, which may comprise or consist of water, distilled water, sterile water, water for irrigation, water for injection, saltwater, sodium chloride (e.g., 0.9%) or saline. In one formulation, the topical composition includes one or both of poloxamers or xylitol. For example, the combined amount of poloxamers and/or xylitol in the topical composition may be between about 10 mg and about 1 g, such as in an amount about 50 mg to about 500 mg, about 100 mg to about 400 mg, or about 150 mg to about 300 mg. In one example, poloxamers, xylitol, or mixture thereof may include LOX- ASPERSE®, which may be combined alone or in combination with one or more additional active ingredients. In one embodiment, the topical composition is configured for combination therapy wherein the steroid is administered separately from the theophylline and sodium citrate.

In one embodiment, the topical composition comprises about 0.25 mg to about 4 mg budesonide, about 20 mg to about 200 mg, such as about 50 mg to about 150 mg, or about 75 mg to about 100 mg, theophylline, and/or about 5 mg to about 150 mg, such as about 10 mg to about 50 mg, or about 50 mg to about 100 mg, sodium citrate. The topical composition may also include one or more of about 10 mg to about 1 g antihistamine or about 5 mg to 500 mg mucolytic. In one example, the antihistamine comprises about 100 mg to about 1 g azelastine. In this or another example, the mucolytic comprises about 15 mg to about 250 mg acetylcysteine. In one example, the topical composition may further include a diluent, e.g., as disclosed herein, such as an aqueous diluent, which may comprise or consist of water, distilled water, sterile water, water for irrigation, water for injection, saltwater, sodium chloride (e.g., 0.9%) or saline. In one formulation, the topical composition includes one or both of poloxamers or xylitol. For example, the combined amount of poloxamers and/or xylitol in the topical composition may be between about 10 mg and about 1 g, such as in an amount about 50 mg to about 500 mg, about 100 mg to about 400 mg, or about 150 mg to about 300 mg. In one example, poloxamers, xylitol, or mixture thereof may include LOXASPERSE®, which may be combined alone or in combination with one or more additional active ingredients. In one embodiment, the topical composition is configured for combination therapy wherein the steroid is administered separately from the theophylline and sodium citrate.

In one embodiment, the topical composition comprises about 1 mg to about 10 mg methylprednisolone, about 20 mg to about 200 mg, such as about 50 mg to about 150 mg, or about 75 mg to about 100 mg, theophylline, and/or about 5 mg to about 150 mg, such as about 10 mg to about 50 mg, or about 50 mg to about 100 mg, sodium citrate. In a further embodiment, the topical composition includes about 10 mg to about 1 g antihistamine or about 5 mg to 500 mg mucolytic. In one example, the antihistamine comprises about 100 mg to about 1 g azelastine. In this or another example, the mucolytic comprises about 15 mg to about 250 mg acetylcysteine. In one example, the topical composition may further include a diluent, e.g., as disclosed herein, such as an aqueous diluent, which may comprise or consist of water, distilled water, sterile water, water for irrigation, water for injection, saltwater, sodium chloride (e.g., 0.9%) or saline. In one formulation, the topical composition includes one or both of poloxamers or xylitol. For example, the combined amount of poloxamers and/or xylitol in the topical composition may be between about 10 mg and about 1 g, such as in an amount about 50 mg to about 500 mg, about 100 mg to about 400 mg, or about 150 mg to about 300 mg. In one example, poloxamers, xylitol, or mixture thereof may include LOXASPERSE®, which may be combined alone or in combination with one or more additional active ingredients. In one embodiment, the topical composition is configured for combination therapy wherein the steroid is administered separately from the theophylline and sodium citrate.

In one embodiment, a method of non-infective nasal symptom management includes nasal administration of a topical composition comprising a steroid. The steroid may comprise or consist of one or more steroids selected from, but not limited to: triamcinolone (e.g., diacetate, hexacetonide, and acetonide), betamethasone (e.g., dipropionate, benzoate, sodium phosphate, acetate, and valerate), dexamethasone (e.g., dipropionate and valerate), flunisolide, prednisone (e.g., acetate), prednisolone (e.g., acetate, sodium phosphate, and tebutate), methylprednisolone (e.g., acetate and sodium succinate), fluocinolone (e.g., acetonide), budesonide, diflorasone (e.g., diacetate), halcinonide, desoximetasone (desoxymethasone), diflucortolone (e.g., valerate), flucloronide (fluclorolone acetonide), fluocinonide, fluocortolone, fluprednidene (e.g., acetate), flurandrenolide (flurandrenolone), clobetasol (e.g., propionate), clobetasone (e.g., butyrate), alclometasone, flumethasone (e.g., pivalate), fluocortolone (e.g., hexanoate), amcinonide, beclometasone (e.g., dipropionate), fluticasone (e.g., propionate), difluprednate, prednicarbate, flurandrenolide, mometasone, and desonide.

In various embodiments, the topical composition or a method of non-infective nasal symptom management may include combining and/or administering the components of the topical composition for nasal administration, wherein the components include a steroid selected from one or more of the above steroids in an amount about 0.25 mg to about 10 mg, such as about 0.5 mg to about 8 mg, about 1 mg to about 6 mg, about 2 mg to about 5 mg, about 3 mg to about 5 mg, about 4 mg to about 6 mg, about 5 mg to about 7 mg, about 6 mg to about 9 mg, about 6 mg to about 10 mg, about 0.25 mg to about 5 mg, about 0.5 mg to about 5 mg, about 0.5 mg to about 3 mg, about 0.5 to about 2 mg, about 2 mg to about 3 mg, about 3 mg to about 4 mg, about 0.25 mg, about 0.5 mg, about 1 mg, about 1.25 mg, about 1.5 mg, about 1.75 mg, about 2 mg, about 3 mg, about 4 mg, about 5 mg, about 6 mg, or about 7 mg. The steroid may be combined or administered in a steroid solution, suspension, emulsion, or powder.

The topical composition may include the diluent or be combined, e.g., added together with the diluent and mixed to form a solution, mixture, emulsion, or suspension, for example, wherein the steroid and/or other actives or ingredients are mixed, dissolved, suspended, dispersed, or otherwise within the diluent. The diluent may comprise an aqueous diluent such as water, distilled water, sterile water, water for irrigation, water for injection, saltwater, sodium chloride (e.g., 0.9%) or saline.

The topical composition may be formulated for administration nasally, e.g., as a powder, by intranasal irrigation or nebulization. In various embodiments, a method of making the topical composition may include mixing the steroid with the diluent. The diluent may be mixed in an amount suitable for the manner of administration. For example, administration volumes for nebulizer solutions may typically range from about 0.2 ml to about 15 ml while irrigation volumes may typically range from about 20 ml to about 500 ml. In an above or another embodiment, the topical composition may include one or both of poloxamers or xylitol. The method may include combining the steroid, and poloxamers, xylitol, or mixture thereof with diluent and mixing. In some embodiments, the poloxamers, xylitol, or mixture thereof includes LOXASPERSE® and the method includes also combining the LOXASPERSE® with the diluent and steroid and mixing. In various embodiments, LOXASPERSE® may be added in an amount about 100 mg to 1 g, e.g., about 500 mg. Dosing may be 1 to 3 times a day or as otherwise needed.

Combining and mixing may be performed in a mixing container. In some examples, combining and mixing may beneficially be performed within an irrigation system vessel or nebulization vessel. As used herein, combining includes mixing.

In various embodiments, the steroid comprises or consists of at least one of fluticasone, budesonide, or methylprednisolone.

In one embodiment, the steroid comprises or consists of fluticasone. For example, the topical composition or the method of non-infective nasal system management may include formulating the topical composition to include fluticasone in an amount about 0.5 mg to about 6 mg, about 1 mg to about 5 mg, about 2 mg to about 4 mg, about 2 mg to about 3 mg, about 3 mg to about 4 mg, or about 3 mg. The fluconazole may include a fluconazole solution, suspension, emulsion, or powder. In one example, to formulate a nebulization or irrigation dosage formulation including 3 mg of fluticasone, the 3 mg of fluticasone powder may be combined with a suitable amount of diluent and mixed. In one embodiment, the diluent comprises distilled water. In one of the above or another embodiment, the topical composition includes one or both of poloxamers or xylitol. For example, the combined amount of poloxamers and/or xylitol may be between about 10 mg and about 1 g, such as in an amount about 50 mg to about 500 mg, about 100 mg to about 400 mg, or about 150 mg to about 300 mg. The method may include combining the steroid, and poloxamers, xylitol, or mixture thereof with diluent and mixing. In some embodiments, the poloxamers, xylitol, or mixture thereof includes LOXASPERSE® and the method includes also combining the LOXASPERSE® with the diluent and fluticasone and mixing. In various embodiments, LOXASPERSE® may be added in an amount about 100 mg to 1 g, e.g., about 500 mg. In some embodiments, the method may include combining or administering additional components of the topical composition comprising about 20 mg to about 200 mg, such as about 50 mg to about 150 mg, or about 75 mg to about 100 mg, theophylline, and/or about 5 mg to about 150 mg, such as about 10 mg to about 50 mg, or about 50 mg to about 100 mg, sodium citrate.

In one embodiment, the steroid comprises or consists of budesonide. For example, the topical composition or the method of non-infective nasal system management may include formulating the topical composition to include budesonide in an amount about 0.25 mg to about 4 mg, about 0.25 mg to about 3 mg, about 0.25 mg to about 2 mg, about 0.5 mg to about 2 mg, about 0.5 mg to about 1 mg, about 1 mg to about 2 mg, about 0.5 mg, about 1 mg, or about 2 mg. The budesonide may include a budesonide solution, suspension, emulsion, or powder. In some embodiments, the method may include formulating the topical composition and/or administering additional components of the topical composition comprising about 20 mg to about 200 mg, such as about 50 mg to about 150 mg, or about 75 mg to about 100 mg, theophylline, and/or about 5 mg to about 150 mg, such as about 10 mg to about 50 mg, or about 50 mg to about 100 mg, sodium citrate.

In various embodiments, the method may comprise utilizing the contents of one or more commercially available budesonide vials. Budesonide vials contain 2 ml of sterile liquid suspension including 0.25 mg, 0.5 mg, and 1 mg budesonide. Budesonide inhalation suspension, for example, may contain micronized budesonide, sodium chloride, disodium edetate, polysorbate 80, citric acid, tri-sodium citrate, and water for injection. In one example, the method may include combining one or more budesonide 0.5 mg-2 ml vials, 1 mg-2 ml vials, or 1 mg-2 ml vials with a suitable amount of diluent to formulate a nebulization or irrigation dosage formulation and mixing. For example, to formulate a nebulization or irrigation dosage formulation including 0.5 mg budesonide, the contents of a budesonide 0.5 mg-2 ml vial may be combined with diluent and mixed. Similarly, to formulate a nebulization or irrigation dosage formulation including 1 mg budesonide, the contents of a budesonide 1 mg-2 ml vial may be combined with diluent and mixed. Multiples of budesonide vials may also be used to make dosage formulations with higher unit doses of budesonide than provided by the contents of a vial. In some embodiments, fractions of a vial may also be used for administration dosage formulations with lower doses of budesonide than provide by the contents of a vial. In one embodiment, the diluent comprises distilled water. In one of the above or another embodiment, the topical composition includes one or both of poloxamers or xylitol. The method may include combining the steroid, and poloxamers, xylitol, or mixture thereof with diluent and mixing. For example, the combined amount of poloxamers and/or xylitol may be between about 10 mg and about 1 g, such as in an amount about 50 mg to about 500 mg, about 100 mg to about 400 mg, or about 150 mg to about 300 mg. In some embodiments, the poloxamers, xylitol, or mixture thereof includes LOXASPERSE® and the method includes also combining the LOXASPERSE® with the diluent and budesonide and mixing. In various embodiments, LOXASPERSE® may be added in an amount about 100 mg to 1 g, e.g., about 500 mg. In some embodiments, the method may include combining and/or administering additional components of the topical composition comprising about 20 mg to about 200 mg, such as about 50 mg to about 150 mg, or about 75 mg to about 100 mg, theophylline, and/or about 5 mg to about 150 mg, such as about 10 mg to about 50 mg, or about 50 mg to about 100 mg, sodium citrate. In one example, theophylline and sodium citrate powder may be provided in a compounded capsule. The contents of the capsule may be combined with the budesonide. In further examples, combining the components may also include combining one or more of a diluent, poloxamers, or xylitol as described herein.

In some embodiments, a method of managing non-infective nasal symptoms includes combining budesonide, a diluent, and about 15 mg to about 250 mg acetylcysteine, about 100 mg to about 1 g azelastine, or about 15 mg to about 250 mg theophylline. The method may further include mixing the combined budesonide, diluent, and acetylcysteine, azelastine, or theophylline to formulate a topical composition for nasal administration via inhalation powder or intranasal irrigation or nebulization. In a further embodiment, the method may include combining about 5 mg to about 150 mg, such as about 10 mg to about 30 mg, about 25 mg to about 50 mg, or about 50 mg to about 100 mg, sodium citrate. In the above or another embodiment, the method includes combining the theophylline in an amount about 20 mg to about 200 mg, such as about 50 mg to about 150 mg, or about 75 mg to about 100 mg, theophylline. The combining of the budesonide may include combining contents of one or more budesonide 0.5 mg-2 ml vials or one or more budesonide 1 mg-2 ml vials. In one example, the combining of the budesonide may include combining the contents of one or more budesonide 0.5 mg-2 ml vials and/or one or more budesonide 1 mg-2 ml vials. In the above or another example, combining the contents of a budesonide vial may include combining the contents of multiple budesonide 0.5 mg-2 ml vials, multiple budesonide 1 mg-2 ml vials, or a combination thereof. In one example, theophylline and sodium citrate powder may be provided in a compounded capsule. The contents of the capsule may be combined with the budesonide. In further examples, combining the components may also include combining one or more of a diluent, poloxamers, or xylitol as described herein. For example, the combined amount of poloxamers and/or xylitol may be between about 10 mg and about 1 g, such as in an amount about 50 mg to about 500 mg, about 100 mg to about 400 mg, or about 150 mg to about 300 mg.

In one embodiment, the steroid comprises or consists of methylprednisolone. For example, the topical composition or the method of non-infective nasal system management may include formulating the topical composition to include methylprednisolone in an amount about 1 mg to about 10 mg, about 2 mg to about 9 mg, about 3 mg to about 8 mg, about 4 mg to about 7 mg, about 4 mg to about 6 mg, about 4 mg to about 5 mg, about 4 mg, about 5 mg, about 6 mg, or about 8 mg. The methylprednisolone may include a methylprednisolone solution, suspension, emulsion, or powder. In one embodiment, the method may comprise combining methylprednisolone powder with a suitable amount of diluent to formulate a nebulization or irrigation solution and mixing. For example, about 5 mg of methylprednisolone powder may be combined with diluent and mixed. In one embodiment, the diluent comprises distilled water. In one of the above or another embodiment, the topical composition includes one or both of poloxamers or xylitol. For example, the combined amount of poloxamers and/or xylitol may be between about 10 mg and about 1 g, such as in an amount about 50 mg to about 500 mg, about 100 mg to about 400 mg, or about 150 mg to about 300 mg. The method may include combining the steroid, and poloxamers, xylitol, or mixture thereof with diluent and mixing. In some embodiments, the poloxamers, xylitol, or mixture thereof includes LOXASPERSE® and the method includes also combining the LOXASPERSE® with the diluent and methylprednisolone and mixing. In various embodiments, LOXASPERSE® may be added in an amount about 100 mg to 1 g, e.g., about 500 mg. In some embodiments, the method may include combining and/or administering additional components of the topical composition comprising about 20 mg to about 200 mg, such as about 50 mg to about 150 mg, or about 75 mg to about 100 mg, theophylline, and/or about 5 mg to about 150 mg, such as about 10 mg to about 50 mg, or about 50 mg to about 100 mg, sodium citrate. In one example, theophylline and sodium citrate powder may be provided in a compounded capsule. The contents of the capsule may be combined with the methylprednisolone. In further examples, combining the components may also include combining one or more of a diluent, poloxamers, or xylitol as described herein.

In one embodiment, the method of non-infective nasal symptom management may include formulating the topical composition to include one or more antihistamines in addition to the one or more of the above steroids in a listed amount. For example, the method may include combining with the steroid one or more antihistamines comprising acrivastine, azelastine, bilastine, bromodiphenhydramine, brompheniramine, buclizine, carbinoxamine, cetirizine, chlorodiphenhydramine, chlorphenamine, chlorpheniramine, chlorpromazine, cimetidine, clemastine, cyclizine, cyproheptadine, desloratadine, dexbrompheniramine, dexchlorpheniramine, dimenhydrinate, dimetindene, diphenhydramine, doxylamine, ebastine, embramine, emedastine, famotidine, fexofenadine, hydroxyzine, lafutidine, levocabastine, loratadine, meclozine, mirtazapine, nizatidine, olopatadine, orphenadrine, phenindamine, pheniramine, phenyltoloxamine, promethazine, pyrilamine, quetiapine, ranitidine, roxatidine, rupatadine, tiotidine, tripelennamine, or triprolidine. The antihistamines may be combined in an amount about 10 mg to about 1 g, about 10 mg to about 500 mg, about 15 mg to about 300 mg, about 25 mg to about 300 mg, about 50 mg to about 250 mg, about 75 mg to about 200 mg, about 100 mg to about 900 mg, about 200 mg to about 800 mg, about 300 mg to about 700 mg, about 400 mg to about 700 mg, or about 500 mg to about 800 mg. The antihistamine may include an antihistamine solution, suspension, emulsion, or powder. The antihistamine may be combined and mixed with the steroid and diluent as described above to formulate a topical composition comprising a inhalation powder, nebulization or irrigation dosage formulation. In some embodiments, the topical composition may include the antihistamine in addition to the steroid and one or more of a mucolytic, theophylline, sodium citrate, anticholinergic, anti-inflammatory, or leukotriene receptor antagonist disclosed herein.

In one embodiment, the antihistamine comprises or consists of azelastine powder in an amount about 100 mg to 1000 mg, about 200 mg to about 900 mg, 300 mg to about 800 mg, 400 mg to about 700 mg, 400 mg to about 600 mg, 500 mg to about 600 mg, about 400 mg, about 500 mg, or about 500 mg.

In one example, a method of making the topical composition comprising a nebulization or irrigation dosage formulation comprising about 500 mg azelastine and about 3 mg fluconazole comprises combining the contents of a capsule containing about 500 mg of azelastine powder with the contents of a capsule containing about 3 mg fluconazole and a suitable amount of diluent, e.g., distilled water, and mixing. In a further example, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as the azelastine and fluconazole.

In another example, a method of making the topical composition comprising a nebulization or irrigation dosage formulation comprising about 500 mg azelastine and about 2 mg of budesonide comprises combining the contents of a capsule containing about 500 mg of azelastine powder with the contents of two budesonide 1 mg-2 ml vials and a suitable amount of diluent, e.g., distilled water, and mixing. In still another example, a method of making the topical composition comprising a nebulization or irrigation dosage formulation comprising about 500 mg azelastine and about 1 mg of budesonide comprises combining the contents of a capsule containing about 500 mg of azelastine powder with the contents of a budesonide 1 mg-2 ml vial and mixing. In a further embodiment, a suitable amount of diluent, e.g., distilled water, may also be added and mixed. In yet another example, a method of making the topical composition comprising a nebulization or irrigation dosage formulation comprising about 500 mg azelastine and about 0.5 mg of budesonide comprises combining the contents of a capsule containing about 500 mg of azelastine powder with the contents of a budesonide 0.5 mg-2 ml vials and a suitable amount of diluent, e.g., distilled water, and mixing. In any of the above examples, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as the azelastine.

In still yet another example, a method of making the topical composition comprising a nebulization or irrigation dosage formulation comprising about 500 mg azelastine and about 5 mg of methylprednisolone comprises combining the contents of a capsule containing about 500 mg of azelastine powder with the contents of a capsule containing about 5 mg of methylprednisolone and a suitable amount of diluent, e.g., distilled water, and mixing. In a further example, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as the azelastine and/or methylprednisolone, e.g., the theophylline, sodium citrate, azelastine, and methylprednisolone may be provided in a single capsule or multiple capsules including any combination of the ingredients.

In one of the above or another embodiment, the topical composition includes steroid, antihistamine, one or both of poloxamers or xylitol. In some embodiments, the topical composition may also include a diluent. The method may include combining the steroid, antihistamine, and poloxamers, xylitol, or mixture thereof with diluent and mixing. For example, the combined amount of poloxamers and/or xylitol may be between about 10 mg and about 1 g, such as in an amount about 50 mg to about 500 mg, about 100 mg to about 400 mg, or about 150 mg to about 300 mg. In some embodiments, the poloxamers, xylitol, or mixture thereof includes LOXASPERSE® and the method includes also combining the LOXASPERSE® with the diluent, steroid, and antihistamine and mixing. In various embodiments, LOXASPERSE® may be added in an amount about 100 mg to 1 g, for example, about 500 mg. In one example, the LOXASPERSE® may be provided in a separate capsule or together with one or both of the steroid or antihistamine or another ingredient. Dosing may be 1 to 3 times a day or as otherwise needed. In a further example, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as one or more of the additional ingredients.

In one embodiment, the method of non-infective nasal symptom management may include formulating the topical composition to include one or more mucolytics in addition to the one or more of the above steroids in a listed amount. For example, the method may include combining with the steroid one or more mucolytics comprising selected from acetylcysteine, bromheksin, carbocysteine, erdosteine, guiafenesin, and iodinated glycerol, or pharmaceutically acceptable salts thereof, or a combination thereof.

In some embodiments, the topical composition includes any of the steroids and associate amounts of steroid identified above and elsewhere herein and one or more of the above mucolytics in an amount about 5 mg to about 500 mg, about 15 mg to about 400 mg, about 50 mg to about 300 mg, about 75 mg to about 200 mg, about 75 mg to about 150 mg, about 100 mg to about 250 mg, about 200 mg to about 500 mg. The mucolytic may include a mucolytic solution, suspension, emulsion, or powder. The mucolytic may be combined and mixed with the steroid and diluent as described above to formulate a topical composition comprising an inhalation powder, a nebulization or irrigation dosage formulation. In some embodiments, the topical composition may include a mucolytic in addition to the steroid and one or more of an antihistamine, anticholinergic, theophylline, sodium citrate, anti-inflammatory, or leukotriene receptor antagonist disclosed herein.

In one embodiment, the mucolytic comprises acetylcysteine in an amount about 15 mg to about 250 mg, about 25 mg to about 200 mg, about 50 mg to about 150 mg, about 75 mg to about 125 mg, or about 100 mg.

In one example, a method of making the topical composition comprising a nebulization or irrigation dosage formulation comprising about 100 mg acetylcysteine and about 3 mg fluconazole comprises combining the contents of a capsule containing about 100 mg of acetylcysteine powder with the contents of a capsule containing about 3 mg fluconazole and a suitable amount of diluent, e.g., distilled water, and mixing. In a further example, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as one or more of the additional ingredients.

In another example, a method of making the topical composition comprising a nebulization or irrigation dosage formulation comprising about 100 mg acetylcysteine and about 2 mg of budesonide comprises combining the contents of a capsule containing about 100 mg of acetylcysteine powder with the contents of two budesonide 1 mg-2 ml vials and a suitable amount of diluent, e.g., distilled water, and mixing. In a further example, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as one or more of the additional ingredients.

In still another example, a method of making the topical composition comprising a nebulization or irrigation dosage formulation comprising about 100 mg acetylcysteine and about 1 mg of budesonide comprises combining the contents of a capsule containing about 100 mg of acetylcysteine powder with the contents of a budesonide 1 mg-2 ml vial, and a suitable amount of diluent, e.g., distilled water, and mixing. In a further example, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as one or more of the additional ingredients.

In yet another example, a method of making the topical composition comprising a nebulization or irrigation dosage formulation comprising about 100 mg acetylcysteine and about 0.5 mg of budesonide comprises combining the contents of a capsule containing about 100 mg of acetylcysteine powder with the contents of a budesonide 0.5 mg-2 ml vials and a suitable amount of diluent, e.g., distilled water, and mixing. In a further example, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as one or more of the additional ingredients.

In still yet another example, a method of making the topical composition comprising a nebulization or irrigation dosage formulation comprising about 100 mg acetylcysteine and about 5 mg of methylprednisolone comprises combining the contents of a capsule containing about 100 mg of acetylcysteine powder with the contents of a capsule containing about 5 mg of methylprednisolone and a suitable amount of diluent, e.g., distilled water, and mixing. In a further example, the method further includes combining about 5 mg to about 150 mg, such as about 10 mg to about 30 mg, about 25 mg to about 50 mg, or about 50 mg to about 100 mg, sodium citrate. In the above or another example, the method further includes combining the theophylline in an amount about 20 mg to about 200 mg, such as about 50 mg to about 150 mg, or about 75 mg to about 100 mg, theophylline. In one example, theophylline and sodium citrate powder may be provided in a compounded capsule, which may be the same or different capsule as one or more of the additional ingredients.

In one of the above or another embodiment, the topical composition includes steroid, mucolytic, diluent, one or both of sodium citrate or theophylline, and one or both of poloxamers or xylitol. For example, the combined amount of poloxamers and/or xylitol may be between about 10 mg and about 1 g, such as in an amount about 50 mg to about 500 mg, about 100 mg to about 400 mg, or about 150 mg to about 300 mg. The method may include combining the steroid, mucolytic, and poloxamers, xylitol, or mixture thereof with diluent and mixing. In one embodiment, the topical composition comprises an inhalation powder, nebulizer solution, spray solution, or irrigation solution. In some embodiments, the poloxamers, xylitol, or mixture thereof includes LOXASPERSE® and the method includes also combining the LOXASPERSE® with the diluent, steroid, and antihistamine and mixing. In various embodiments, LOXASPERSE® may be added in an amount about 100 mg to 1 g, for example, about 500 mg. In one example, the LOXASPERSE® may be provided in a separate capsule or together with one or both of the steroid or mucolytic or another ingredient such as sodium citrate and/or theophylline, when present. Dosing may be 1 to 3 times a day or as otherwise needed.

In one embodiment, the method of non-infective nasal symptom management may include formulating the topical composition to include theophylline in addition to the one or more of the above steroids in a listed amount. For example, the method may include combining theophylline with the steroid. In some embodiments, the method includes formulating the topical composition to includes any of the steroids and associate amounts of steroid identified above and elsewhere herein and theophylline in an amount about 15 mg to about 250 mg, about 25 mg to about 200 mg, about 50 mg to about 150 mg, about 75 mg to about 125 mg, or about 100 mg. Theophylline may include a theophylline solution, suspension, emulsion, or powder. The theophylline may be combined and mixed with the steroid and diluent as described above to formulate a topical composition comprising a nebulization or irrigation dosage formulation or may be administered as a inhalation powder. In some embodiments, the topical composition may include theophylline in addition to the steroid and one or more of an antihistamine, mucolytic, sodium citrate, anticholinergic, anti-inflammatory, or leukotriene receptor antagonist disclosed herein.

In one example, a method of making the topical composition comprising a nebulization or irrigation dosage formulation comprising about 100 mg theophylline and about 3 mg fluconazole comprises combining the contents of a capsule containing about 100 mg of theophylline powder with the contents of a capsule containing about 3 mg fluconazole and a suitable amount of diluent, e.g., distilled water, and mixing. In a further example, the topical composition may further include about 10 mg to about 150 mg, such about 10 to about 50 mg, about 50 mg to about 100 mg, or about 25 mg, sodium citrate. The sodium citrate may comprise a powder provided together with one or more other ingredients or separate in one or more capsules.

In another example, a method of making the topical composition comprising a nebulization or irrigation dosage formulation comprising about 100 mg theophylline and about 2 mg of budesonide comprises combining the contents of a capsule containing about 100 mg theophylline powder with the contents of two budesonide 1 mg-2 ml vials and a suitable amount of diluent, e.g., distilled water, and mixing. In a further example, the topical composition may further include about 10 mg to about 150 mg, such about 10 to about 50 mg, about 50 mg to about 100 mg, or about 25 mg, sodium citrate. The sodium citrate may comprise a powder provided together with one or more other ingredients or separate in one or more capsules.

In still another example, a method of making the topical composition comprising a nebulization or irrigation dosage formulation comprising about 100 mg theophylline and about 1 mg of budesonide comprises combining the contents of a capsule containing about 100 mg of theophylline powder with the contents of a budesonide 1 mg-2 ml vial, and a suitable amount of diluent, e.g., distilled water, and mixing. In a further example, the topical composition may further include about 10 mg to about 150 mg, such about 10 to about 50 mg, about 50 mg to about 100 mg, or about 25 mg, sodium citrate. The sodium citrate may comprise a powder provided together with one or more other ingredients or separate in one or more capsules.

In yet another example, a method of making the topical composition comprising a nebulization or irrigation dosage formulation comprising about 100 mg theophylline and about 0.5 mg of budesonide comprises combining the contents of a capsule containing about 100 mg of theophylline powder with the contents of a budesonide 0.5 mg-2 ml vials and a suitable amount of diluent, e.g., distilled water, and mixing. In a further example, the topical composition may further include about 10 mg to about 150 mg, such about 10 to about 50 mg, about 50 mg to about 100 mg, or about 25 mg, sodium citrate. The sodium citrate may comprise a powder provided together with one or more other ingredients or separate in one or more capsules.

In still yet another example, a method of making the topical composition comprising a nebulization or irrigation dosage formulation comprising about 100 mg theophylline and about 5 mg of methylprednisolone comprises combining the contents of a capsule containing about 100 mg of theophylline powder with the contents of a capsule containing about 5 mg of methylprednisolone and a suitable amount of diluent, e.g., distilled water, and mixing. In a further example, the topical composition may further include about 10 mg to about 150 mg, such about 10 to about 50 mg, about 50 mg to about 100 mg, or about 25 mg, sodium citrate. The sodium citrate may comprise a powder provided together with one or more other ingredients or separate in one or more capsules.

In one of the above or another embodiment, the topical composition includes steroid, theophylline, diluent, and one or both of poloxamers or xylitol. For example, the combined amount of poloxamers and/or xylitol may be between about 10 mg and about 1 g, such as in an amount about 50 mg to about 500 mg, about 100 mg to about 400 mg, or about 150 mg to about 300 mg. The method may include combining the steroid, theophylline, and poloxamers, xylitol, or mixture thereof with diluent and mixing. In some embodiments, the poloxamers, xylitol, or mixture thereof includes LOXASPERSE® and the method includes also combining the LOXASPERSE® with the diluent, steroid, and theophylline and mixing. In various embodiments, LOXASPERSE® may be added in an amount about 100 mg to 1 g, for example, about 500 mg. In one example, the LOXASPERSE® may be provided in a separate capsule or together with one or both of the steroid or theophylline or another ingredient. In a further example, the topical composition may further include about 10 mg to about 150 mg, such about 10 to about 50 mg, about 50 mg to about 100 mg, or about 25 mg, sodium citrate. The sodium citrate may comprise a powder provided together with one or more other ingredients or separate in one or more capsules. Dosing may be 1 to 3 times a day or as otherwise needed.

In one embodiment, the method of non-infective nasal symptom management may include formulating the topical composition to include quinine sulfate in addition to the steroid, e.g., one or more of the above steroids, in a listed amount. For example, the method may include addition of quinine sulfate with the steroid theophylline. In some embodiments, the method includes formulating the topical composition to includes any of the steroids and associated amounts of steroid identified above and elsewhere herein and quinine sulfate in an amount about 50 mg to about 1000 mg, about 50 mg to about 700 mg, about 50 mg to about 500 mg, about 50 mg to about 350 mg, about 100 mg to about 325 mg, about 100 mg to about 200 mg, about 200 mg to about 350 mg, about 250 mg to about 325 mg, about 150 mg to about 300 mg, about 275 mg to about 325 mg, about 100 mg to about 700 mg, about 200 mg to about 500 mg, about 300 mg to about 400 mg, about 300 mg to about 700 mg, about 400 mg to about 700 mg, about 500 mg to about 700 mg, about 600 mg to about 700 mg, or about 325 mg or about 650 mg. Quinine sulfate may include a quinine sulfate solution, suspension, emulsion, tablet, capsule, or powder. Quinine sulfate may include commercially available quinine sulfate, e.g., quinine sulfate solution, suspension, emulsion, capsule, table or powder. The quinine sulfate may be combined and mixed with the steroid and diluent as described above to formulate a topical composition comprising a nebulization or irrigation dosage formulation for nasal administration. In some embodiments, the topical composition may include quinine sulfate in addition to the steroid and one or more of an antihistamine, mucolytic, anticholinergic, anti-inflammatory, theophylline, or leukotriene receptor antagonist disclosed herein.

In one example, a method of making the topical composition comprising a nebulization or irrigation dosage formulation comprising up to about 325 mg quinine sulfate and about 3 mg fluconazole comprises combining the contents or an equivalent portion thereof of a 324 mg quinine sulfate capsule with the contents of a capsule containing about 3 mg fluconazole and a suitable amount of diluent, e.g., distilled water or saline solution, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein.

In another example, a method of making the topical composition comprising a nebulization or irrigation dosage formulation comprising up to about 325 mg quinine sulfate and about 2 mg of budesonide comprises combining the contents or equivalent portion thereof of a 324 mg quinine sulfate capsule with the contents of two budesonide 1 mg-2 ml vials and a suitable amount of diluent, e.g., distilled water, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein.

In still another example, a method of making the topical composition comprising a nebulization or irrigation dosage formulation comprising up to about 325 mg quinine sulfate and about 1 mg of budesonide comprises combining the contents or an equivalent portion thereof of a 324 mg quinine sulfate capsule with the contents of a budesonide 1 mg-2 ml vial, and a suitable amount of diluent, e.g., distilled water, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. In some embodiments, the method may include combining additional ingredients of the topical composition comprising about 20 mg to about 200 mg, such as about 50 mg to about 150 mg, or about 75 mg to about 100 mg, theophylline, and/or about 5 mg to about 150 mg, such as about 10 mg to about 50 mg, about 50 mg to about 100 mg, or about 25 mg, sodium citrate. In one example, theophylline and sodium citrate powder may be provided in one or more compounded capsules together or separate of the additional ingredients. The composition may be delivered nasally as disclosed herein.

In yet another example, a method of making the topical composition comprising a nebulization or irrigation dosage formulation comprising up to about 325 mg quinine sulfate and about 0.5 mg of budesonide comprises combining the contents or an equivalent portion thereof of a 324 mg quinine sulfate capsule with the contents of a budesonide 0.5 mg-2 ml vial and a suitable amount of diluent, e.g., distilled water, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. In some embodiments, the method may include combining additional ingredients of the topical composition comprising about 20 mg to about 200 mg, such as about 50 mg to about 150 mg, or about 75 mg to about 100 mg, theophylline, and/or about 5 mg to about 150 mg, such as about 10 mg to about 50 mg, about 50 mg to about 100 mg, or about 25 mg, sodium citrate. In one example, theophylline and sodium citrate powder may be provided in one or more compounded capsules together or separate of the additional ingredients. The composition may be delivered nasally as disclosed herein.

In still yet another example, a method of making the topical composition comprising a nebulization or irrigation dosage formulation comprising up to about 325 mg quinine sulfate and about 5 mg of methylprednisolone comprises combining the contents or an equivalent portion thereof of a 324 mg quinine sulfate capsule the contents of a capsule containing about 5 mg of methylprednisolone and a suitable amount of diluent, e.g., distilled water, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. In some embodiments, the method may include combining additional ingredients of the topical composition comprising about 20 mg to about 200 mg, such as about 50 mg to about 150 mg, or about 75 mg to about 100 mg, theophylline, and/or about 5 mg to about 150 mg, such as about 10 mg to about 50 mg, about 50 mg to about 100 mg, or about 25 mg, sodium citrate. In one example, theophylline and sodium citrate powder may be provided in one or more compounded capsules together or separate of the additional ingredients. The composition may be delivered nasally as disclosed herein.

In one of the above or another embodiment, the topical composition may include steroid, quinine sulfate, diluent, and one or both of poloxamers or xylitol. For example, the combined amount of poloxamers and/or xylitol may be between about 10 mg and about 1 g, such as in an amount about 50 mg to about 500 mg, about 100 mg to about 400 mg, or about 150 mg to about 300 mg. The method may include combining the steroid, quinine sulfate, and poloxamers, xylitol, or mixture thereof with diluent and mixing.

In some embodiments, the poloxamers, xylitol, or mixture thereof includes LOXASPERSE® and the method includes also combining the LOXASPERSE® with the diluent, steroid, and quinine sulfate and mixing. In various embodiments, LOXASPERSE® may be added in an amount about 100 mg to 1 g, for example, about 500 mg. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein. In one example, the LOXASPERSE® may be provided in a separate capsule or together with one or both of the steroid or quinine sulfate or another ingredient. In some embodiments, the method may include combining additional ingredients of the topical composition comprising about 20 mg to about 200 mg, such as about 50 mg to about 150 mg, or about 75 mg to about 100 mg, theophylline, and/or about 5 mg to about 150 mg, such as about 10 mg to about 50 mg, about 50 mg to about 100 mg, or about 25 mg, sodium citrate. In one example, theophylline and sodium citrate powder may be provided in one or more compounded capsules together or separate of the additional ingredients. Dosing may be 1 to 3 times a day or as otherwise needed.

The topical composition may comprise one or more of the listed active components disclosed herein and may further include an excipient component comprising one or more pharmaceutically acceptable excipients. In other embodiments, however, the formulations consist of the one or more of the listed ingredients and one or more pharmaceutically acceptable excipients. Exemplary excipients may assist in the release, dispersion, solubility, or the delivery of one or more of the active components or modify taste. For example, excipients may include one or more of diluents, dispersants, preservatives, solvents, co-solvents, wetting agents, buffering agents, humectants, permeation enhancer, emollient, sweetening agents, anti-foaming agents, thickening agents, or flavoring agents, for example. Diluents may include water, distilled water, sterile water, water for injection, sodium chloride, or saline solution, for example. The diluent may comprise an aqueous diluent.

In various embodiments, the method of non-infective nasal symptom management comprises nasal administering of the topical composition. For example, the topical composition may be administered via a spray in a liquid solution or dry powder, e.g., inhalation powder. In some embodiments, the topical compositions disclosed herein may be formulated without a liquid diluent for nasal administration in a powder format. In some embodiments, nasal administration may also include nasal/intranasal irrigation or nebulization dosage. Accordingly, the topical composition may comprise or be formulated as spray, powder, irrigation, or nebulizer dosage formulation configured for nasal administration. Such formulations may be configured, for example, for delivery to target sites for treatment by spray, irrigation, or nebulization. For example, the topical composition, when prepared for administration, may be formulated in a unit dose form comprising a treatment solution suitable for administration to the nasal cavity, upper respiratory tract, and in some instances lower respiratory tract. In one embodiment, the topical composition is formulated to be delivered by irrigation at the nasal cavity. In another embodiment, the topical composition is formulated to be delivered by a nebulizer to produce aerosol particles or droplets suitable for inhalation and targeted deposition of such aerosol along the respiratory tract. In some embodiments, the topical composition may be nebulized using a nebulizer configured to produce small or large aerosol particles, with respect to the particle size dispersion generated by the nebulization, e.g., using a Nasoneb, Sinustar, or other suitable nebulizer. Various embodiments may further comprise a fluid, carrier, diluent, which may include delivery vehicles, excipients, or additional active components.

In one embodiment, the topical composition is formulated into a nebulizer formulation for delivery via a small particle nebulizer device or delivery system. The small particle nebulization delivery system may be configured to nebulize the formulation, e.g., solution, to produce small particles or droplets, e.g., having aerosol characteristics, wherein the particle size of the majority of the particles or droplets formed by the nebulization is less than about 10 microns, about 8 microns, about 5 microns, or about 3 microns. For example, in some embodiments, about 60%, 70%, 80%, 90% or greater of the particles or droplets formed by the nebulization are less than about 5 microns. In these or other embodiments, the particles may be produced within a particle size dispersion wherein at least 50%, 60%, 70%, 80%, 90%, or 95% of the particles may be with about 3 microns and about 10 microns, about 3 microns and about 8 microns, about 3 microns and about 5 microns, about 5 microns and about 8 microns, about 5 microns and about 10 microns, or about 8 microns and about 10 microns.

Accordingly, a method of administering the topical composition comprising a nebulizer formulation may comprise using a small particle nebulizer delivery system and nebulizing the formulation to form small particles or droplets. The small particles may then be inhaled into the upper airway and deposit at the paranasal sinus and nasal mucosa. Compared to large particle nebulizer delivery systems, small particle nebulizer delivery systems may be used to deliver a greater fraction of active components to the pulmonary system. This may increase systemic bioavailability of the active components. However, when increased systemic bioavailability is not desirable, e.g., when such bioavailability is linked to unwanted side effects, the formulation may be prepared for and delivered by a large particle nebulizer delivery system. While any suitable small particle nebulizer delivery system or device may be used, one suitable device is a PART or Sinustar intranasal nebulizer.

In one embodiment, the topical composition comprises a nebulizer formulation for delivery via a large particle nebulizer or delivery system. The large particle nebulizer delivery system may include a nebulizer configured to generate particles or droplets wherein the majority of the particles or droplets are larger than about 5 microns, about 10 microns, about 15 microns, about 20 microns or more, such as about 23 microns. In various embodiments, nebulization with a large particle nebulizer produces aerosol particles wherein the majority of particles are greater than about 10 microns, about 15 microns, about 20 microns, or about 25 microns. In these or other embodiments, the particles may be produced within a particle size dispersion wherein at least 50%, 60%, 70%, 80%, 90%, or 95% of the particles may be within about 10 microns and about 25 microns, about 10 microns and about 20 microns, about 10 microns and about 15 microns, about 15 microns and about 25 microns, about 15 microns and about 20 microns, or about 20 microns and about 25 microns. Accordingly, a method of administering the topical composition comprising a nebulizer formulation for large particle nebulization may comprises nebulizing the nebulizer solution to form large particles. The large particles may then be inhaled into the nasal and paranasal sinus cavities and for deposition on the frontal recess/sinus, spheno-ethmoid recess, ethmoid cavity, sphenoid and maxillary sinuses, turbinates, middle meatus, and olfactory cleft. The large particle nebulizer delivery system may be configured to provide low volume, high concentration delivery of the formulation. An exemplary nebulizer device is a NasoNeb® Nasal Nebulizer. Such large particle delivery systems may be employed to deliver a deep, penetrating aerosol to the nasal and paranasal sinus cavities of the patient. Such delivery may include little to no incidental pulmonary delivery of drugs, which may otherwise occur in small particle systems, as described above. For example, in some embodiments, large particle nebulization may provide superior outcomes compared to small particle nebulization to treat the upper respiratory tract, which typically include pulmonary delivery and decreased nasal and paranasal sinus cavity disposition.

In one embodiment, the large particle nebulizer system may be used to nebulize the nebulizer solution to generate large particles for delivery to the respiratory tract via a positive pressure airstream that ensures the components of the composition reach all of the desired nasal and paranasal sinus cavities. The large particle nebulizer system may preferably deliver the large particles such that they are readily filtered by the nose to ensure a large percentage of medication is delivered upon target surfaces where intended and that little or no unintended components of the formulation are delivered to the lungs, thus, reducing the risk of unwanted complications.

In one embodiment, the large particle nebulizer system is configured to deliver a low volume treatment solution comprising the composition to ensure that the active components of the formulation stay in the nasal cavity. Accordingly, such a system may reduce waste generated by irrigation systems. In one embodiment, the large particle nebulizer system is configured to deliver 0.2-15 mL of nebulizer solution comprising the unit dose of active components for retention in the nasal and paranasal sinus cavities. In one embodiment, the large particle nebulization system may also reduce complications associated with repeated exposure to cold fluid irrigation such as exostoses of the paranasal sinus cavities by warming the solution to near room temperature upon nebulization, which may help to avoid the iatrogenic complication of exostoses from cold fluid irrigation.

Administering the nebulizer treatment solution via a large particle nebulizer system may also avoid undesirable complications that may be linked to long-term use of small particle nebulization systems, which may include vocal irritation/alterations, chronic cough, antimicrobial resistance, eosinophilic pneumonia, and reduced lung function.

According to one embodiment, the nebulizer formulation is configured for treatment of allergic rhinitis or other rhinologic conditions.

According to various embodiments, delivery of the formulation via a small particle size delivery system provides penetration of the formulation or its active components into the lower respiratory tract.

The topical composition may also be configured for nasal administration via intranasal irrigation. In such embodiments, the typical mode of administration may be in flush form or liquid stream form. An example of suitable sinus rinse delivery mechanisms include the NeilMed® Sinus Rinse Bottle, a medical syringe of about 20 to about 60 ml in size, and other squeeze bottle irrigation devices. Typically, the formulation is administered two or three times a day. Various forms of irrigation may be used such as high volume, low volume, high pressure, low pressure, or combination thereof. For example, in some embodiments, the topical composition may be administered by low volume, low pressure irrigation. In another example, the topical composition may be administered by high volume, high pressure irrigation.

Effectiveness of the composition for treatment of respiratory tract conditions wherein the composition comprises a treatment solution administered via a Nasoneb, Sinustar, or irrigation system may provide advantages over conventional azelastine hydrochloride nasal spray compositions. For example, administration of the composition via intranasal nebulization, e.g., using a Nasoneb intranasal nebulizer, or with irrigation may provide the ability to increase positive pressure associated with such irrigation or nebulization. Also, if delivered via a large particle nebulization system including a large particle nebulizer device, the composition thereof will reach the paranasal sinus area in lieu of the frontal area where a nasal spray would reach thereby providing additional and enhanced benefits.

In one embodiment, the topical composition comprises or consists of sodium citrate in an amount about 10 mg to about 150 mg, such about 10 to about 50 mg, about 50 mg to about 100 mg, or about 25 mg, and theophylline in an amount about 5 mg to about 150 mg, such as between about 50 mg to about 150 mg, about 75 mg to about 125 mg, or about 100 mg. In a further embodiment, the topical composition comprises or consists of sodium citrate and theophylline, as described above, and a diluent. The diluent may be any suitable diluent, such as those described herein, e.g., an aqueous diluent such as water, distilled water, sterile water, water for irrigation, water for injection, saltwater, sodium chloride (e.g., 0.9%) or saline. In a further embodiment, the topical composition comprises or consists of sodium citrate, theophylline, and a diluent, as described above, and poloxamers and/or xylitol, wherein the poloxamers and/or xylitol are included in a combined amount between about 10 mg and about 1 g, such as in an amount about 50 mg to about 500 mg, about 100 mg to about 400 mg, or about 150 mg to about 300 mg. In some embodiments, the topical composition may further include or exclude one or more of quinine sulfate, an antihistamine, mucolytic, anticholinergic, anti-inflammatory, or leukotriene receptor antagonist as disclosed herein. In one embodiment, all or a portion of the topical composition is administered as an inhalation powder and any remaining portion is administered as a nebulization, irrigation, or spray solution. For example, sodium citrate and theophylline may be administered as an inhalation powder and a steroid may be administered as a nasal nebulization, irrigation, or spray solution. The topical composition may be administered to treat anti-infective nasal conditions described herein, such as anosmia.

In some embodiments, the topical composition may include a combination therapy of two or more separate formulations for administration together, e.g., within about 20 minutes, within about an hour, within about 4 hours, within about 6 hours, within about 12 hours, or within about 24 hours of each other. Administration of separate formulations of the components of the topical composition as a combination therapy may also be referred to as a treatment regimen.

In one embodiment, the topical composition comprises or consists of at least one steroid selected from fluticasone, budesonide, and methylprednisolone, sodium citrate in an amount about 10 mg to about 150 mg, such about 10 to about 50 mg, about 50 mg to about 100 mg, or about 25 mg, theophylline in an amount about 5 mg to about 150 mg, such as between about 50 mg to about 150 mg, about 75 mg to about 125 mg, or about 100 mg. In some examples, the steroid may comprise or consists of about 0.5 mg to about 6 mg fluticasone, about 0.25 mg to about 4 mg budesonide, or about 1 mg to about 10 mg methylprednisolone. In a further embodiment, the topical composition comprises the steroid, sodium citrate, theophylline, and poloxamers and/or xylitol in a combined amount between about 10 mg and about 1 g, such as in an amount about 50 mg to about 500 mg, about 100 mg to about 400 mg, or about 150 mg to about 300 mg. In any of the above, the topical composition may further include a diluent, e.g., as disclosed herein. In one aspect, a method of formulating a topical composition to treat a non-infective nasal symptom in a subject includes formulating the topical composition by combining, e.g., mixing, the ingredients. In some embodiments, the topical composition may include or exclude one or more of quinine sulfate, an antihistamine, mucolytic, anticholinergic, anti-inflammatory, or leukotriene receptor antagonist disclosed herein.

A method of treating a non-infective nasal symptom in a subject may include dispensing one or more capsules containing ingredients of the topical composition for subsequent mixing with a diluent or liquid prior to administration. For example, one or more capsules containing theophylline and sodium citrate may be dispensed. If the topical composition includes additional active agents, such as one or more of quinine sulfate, steroid, antihistamine, mucolytic, anticholinergic, anti-inflammatory, or leukotriene receptor antagonist as disclosed herein, in some embodiments, such additional active agents may be included in the capsules. The capsules may be mixed with a diluent prior to administration. For example, if the topical composition also includes a steroid as described herein, the capsules may include a steroid. The capsules may also include xylitol and/or poloxamers. In an example, the capsule may include theophylline and sodium citrate and, optionally xylitol and/or poloxamers. The capsule may be opened and its contents mixed with contents of a budesonide inhalation suspension vial including 0.25 mg, 0.5 mg, or 1 mg budesonide. In one embodiment, the topical composition is configured for combination therapy wherein one or more additional active agents, such as a steroid, are administered separately from the theophylline and sodium citrate, e.g., theophylline and sodium citrate may be combined with a diluent without a steroid and administered separately from the steroid as part of a combination therapy. Such additional active agent portions may be mixed with a diluent as necessary as described herein. If present, one or both of the theophylline and sodium citrate or other active agent portions, e.g., a steroid portion, may include one or both of poloxamers or xylitol.

A method of treating a non-infective nasal symptom in a subject may include administering the topical composition to the nasal cavity or upper respiratory tract as described herein. In one embodiment, the topical composition is administered as a combination therapy wherein the steroid is administered separately from the theophylline and sodium citrate portions. In another embodiment, the topical composition does not include a steroid and a steroid is not co-administered as part of a combination therapy. The topical composition may be formulated as a nebulization, irrigation, or spray dosage form. The topical composition may be administered to a subject, e.g., human, in need to treat a non-infective nasal condition such as one or more of inflammation in the nasal cavity, thick-mucus secretions in nasal cavity, allergic rhinitis (runny nose), anosmia (inability to smell), or other nasal conditions or related symptoms caused by non-infective conditions.

It is to be appreciated that the examples, embodiments, and other descriptions herein with respect to the topical composition and related methods may specifically exclude any component or ingredient thereof described herein. In some embodiments, the topical composition does not include other components, such as resins, oils, lipids, water, organic solvents, DMSO, alcohol, fatty acids, inorganic solvents, antibodies, proteins, amino acids, nucleic acids, biological tissues, or biological compounds.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y".

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "about" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements disclosed herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of formulating a topical composition comprising theophylline, sodium citrate, an aqueous diluent, and xylitol and/or poloxamers, wherein the method comprises combining:
   theophylline in an amount between about 20 mg and about 200 mg,
   sodium citrate in an amount between about 5 mg and about 150 mg, and
   xylitol and/or poloxamers in an amount between about 50 mg and about 400 mg.

2. The method of claim 1, further comprising combining budesonide.

3. The method of claim 2, wherein the budesonide is combined in an amount between about 1 mg and about 4 mg per unit dose in the topical composition.

4. The method of claim 1, wherein the diluent is distilled water.

5. The method of claim 1, wherein the sodium citrate is an amount between about 10 mg and about 100 mg.

6. The method of claim 5, wherein the theophylline is an amount between about 50 mg and about 150 mg.

7. The method of claim 6, wherein the xylitol and/or poloxamers is in an amount between about 100 mg and about 300 mg.

8. The method of claim 7, further comprising combining budesonide.

9. The method of claim 8, wherein the budesonide is in an amount between about 1 mg and about 4 mg.

10. A topical composition comprising:
    theophylline in an amount between about 20 mg and about 200 mg,
    sodium citrate in an amount between about 5 mg and about 150 mg, and
    xylitol and/or poloxamers in an amount between about 50 mg and about 400 mg.

11. The topical composition of claim 10, further comprising budesonide.

12. The composition of claim 11, wherein the budesonide is in an amount between about 1 mg and about 4 mg.

13. The composition of claim 10, wherein the sodium citrate is an amount between about 10 mg and about 100 mg.

14. The composition of claim 13, wherein the theophylline is an amount between about 50 mg and about 150 mg.

15. The composition of claim 14, wherein the xylitol and/or poloxamers is in an amount between about 100 mg and about 300 mg.

16. The topical composition of claim 15, further comprising budesonide.

17. The composition of claim 16, wherein the budesonide is in an amount between about 1 mg and about 4 mg.

* * * * *